US 7,755,764 B2

(12) United States Patent
Kwak et al.

(10) Patent No.: US 7,755,764 B2
(45) Date of Patent: Jul. 13, 2010

(54) PURGE GAS FLOW CONTROL FOR HIGH-PRECISION FILM MEASUREMENTS USING ELLIPSOMETRY AND REFLECTOMETRY

(75) Inventors: Hidong Kwak, San Jose, CA (US); Shankar Krishnan, Santa Clara, CA (US)

(73) Assignee: KLA-Tencor Corporation, San Jose, CA (US)

( * ) Notice: Subject to any disclaimer, the term of this patent is extended or adjusted under 35 U.S.C. 154(b) by 0 days.

(21) Appl. No.: 12/019,592

(22) Filed: Jan. 24, 2008

(65) Prior Publication Data

US 2008/0180698 A1  Jul. 31, 2008

Related U.S. Application Data

(60) Provisional application No. 60/886,899, filed on Jan. 26, 2007.

(51) Int. Cl.
*G01N 21/55* (2006.01)
(52) U.S. Cl. ............... 356/445; 356/630; 356/600; 356/369; 250/372; 250/373; 250/559.32
(58) Field of Classification Search ............... 356/445, 356/630, 635, 600, 455, 369; 250/372, 373, 250/559.32
See application file for complete search history.

(56) References Cited

U.S. PATENT DOCUMENTS

| 6,813,026 | B2 * | 11/2004 | McAninch | 356/445 |
| 6,945,090 | B2 | 9/2005 | Rodier | 73/24.06 |
| 6,982,792 | B1 | 1/2006 | Woollam et al. | 356/369 |
| 7,126,689 | B2 * | 10/2006 | Nishi | 356/614 |
| 2002/0149774 | A1 | 10/2002 | McAninch | 356/445 |
| 2004/0150820 | A1 | 8/2004 | Nikoonahad et al. | 356/364 |
| 2005/0252752 | A1 | 11/2005 | Fielden et al. | 200/43.04 |
| 2005/0254050 | A1 * | 11/2005 | Fielden et al. | 356/369 |

OTHER PUBLICATIONS

U.S. Appl. No. 60/886,899 filed Jan. 26, 2007.
International Search Report and Written Opinion of the International Searching Authority dated Jul. 9, 2008—International application No. PCT/US08/52118.

* cited by examiner

*Primary Examiner*—Gregory J Toatley, Jr.
*Assistant Examiner*—Iyabo S Alli
(74) *Attorney, Agent, or Firm*—Joshua D. Isenberg; JDI Patent

(57) ABSTRACT

An optical method and system for measuring characteristics of a sample using a broadband metrology tool in a purge gas flow environment are disclosed. In the method a beam path for the metrology tool is purged with purge gas at a first flow rate. A surface of the sample is illuminated by a beam of source radiation having at least one wavelength component in a vacuum ultraviolet (VUV) range and/or at least one wavelength component in an ultraviolet-visible (UV-Vis) range. A flow rate of a purge gas is adjusted between the first flow rate for metrology measurements made when the source radiation is in the VUV spectral region and a second flow rate for metrology measurements made when the source radiation is in the UV-Vis spectral region. The system includes a light source, illumination optics, collection optics, detector, a purge gas source and a controller. The purge gas source is configured to supply a flow of purge gas to a beam path in the light source and/or illumination optics and/or sample and/or collection optics and/or detector. The controller is configured to control a flow rate of the purged gas flow in response to an output signal from the detector.

20 Claims, 5 Drawing Sheets ered to as Airborne molecular Contaminants or AMC), which results typically in a change to the effective thickness of the AMC layer on wafer during film thickness measurements in the ultraviolet-visible spectral region, causing the precision of the measurement to be higher.

It is within this context that embodiments of the present invention arise.

BRIEF DESCRIPTION OF THE DRAWINGS

Objects and advantages of the invention will become apparent upon reading the following detailed description and upon reference to the accompanying drawings in which.

DESCRIPTION OF THE SPECIFIC EMBODIMENTS

Although the following detailed description contains many specific details for the purposes of illustration, anyone of ordinary skill in the art will appreciate that many variations and alterations to the following details are within the scope of the invention. Accordingly, the exemplary embodiments of the invention described below are set forth without any loss of generality to, and without imposing limitations upon, the claimed invention.

Figure 1:
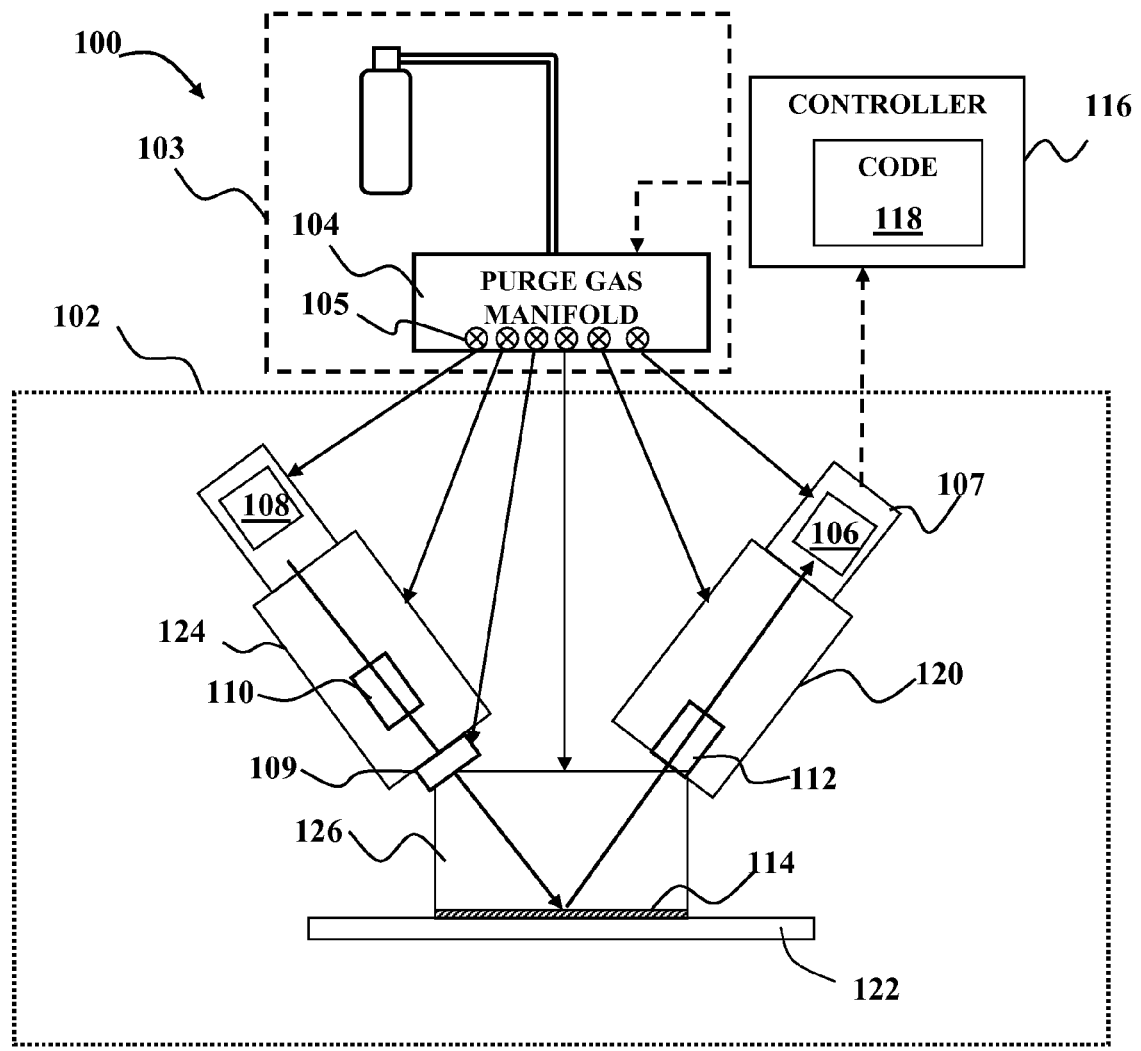
FIG. 1 is a schematic diagram illustrating an optical system for measuring characteristics of a sample using a broadband metrology tool in a purged gas flow environment according to a preferred embodiment of the present invention.

FIG. 1 is a block diagram of an optical system 100 for measuring characteristics of a sample using a broadband metrology tool 102 in a purged gas flow environment according to an embodiment of the present invention. The optical system 100 includes a light source 108, an illumination optics housing 124, illumination optics 110, focus optics located in a focus housing 109, a main housing 126, a collection optics housing 120, collection optics 112 and a detector 106 such as a spectrometer located in a detector housing 107. The light source 108 may be characterized by one or more wavelengths within the electromagnetic spectrum (including but not limited to vacuum ultra violet, ultraviolet, visible, infrared and the like). Preferably, the light source 108 produces source radiation having at least one wavelength component in a vacuum ultraviolet (VUV) range and at least one wavelength component in an ultraviolet-visible (UV-Vis) range.

By way of example, the optical system 100 may be a spectroscopic ellipsometer, a single-wavelength ellipsometer, a spectroscopic reflectometer or a single wavelength reflectometer. Examples of such optical systems include Spectra Fx 100 and Spectra Fx 200 optical thin film metrology systems available from KLA-Tencor Corporation of San Jose, Calif.

The optical system 100 also includes a purge gas source 103 and a controller 116. The purge gas source 103 typically supplies a gas that does not substantially absorb VUV radiation, such as nitrogen, argon, neon and other inert gases. The controller 116 is operably coupled to the gas source 103 and the detector 106 in a feedback loop to control purge gas flow rates to the focus housing 109, illumination optics housing 124, collection optics housing 120, the main housing 126 and detector housing 107. The controller 116 may be configured to control separate flows of purge gas to two or more of the light source 108, focus housing 109, illumination optics housing 124, main housing 126, collection optics housing 120 and/or detector housing 107. By way of example and without limitation, the gas source 103 may include a gas manifold 104 to facilitate supply of purge gas to different portions of a beam path for the system 100. The gas manifold 104 may be coupled to two or more of the light source 108, illumination optics housing 124, main housing 126, collection optics housing 120 and/or detector housing 107 through separate gas lines. Each gas line may have a valve 105 operably coupled to the controller 116. The valves 105 may open, close or throttle gas flow through them in response to signals from the controller 116.

The controller 116 may operate in response to code instructions 118, which include instructions that direct the purge gas source 103 to adjust the flow rate of purged gas into the focus housing 109, illumination optics housing 124, collection optics housing 120, the main housing 126 and detector housing 107. As shown in FIG. 1, a stage 122 holding a sample 114, such as a semiconductor wafer, is positioned in the main housing 126 for optical metrology measurement.

Figure 2:
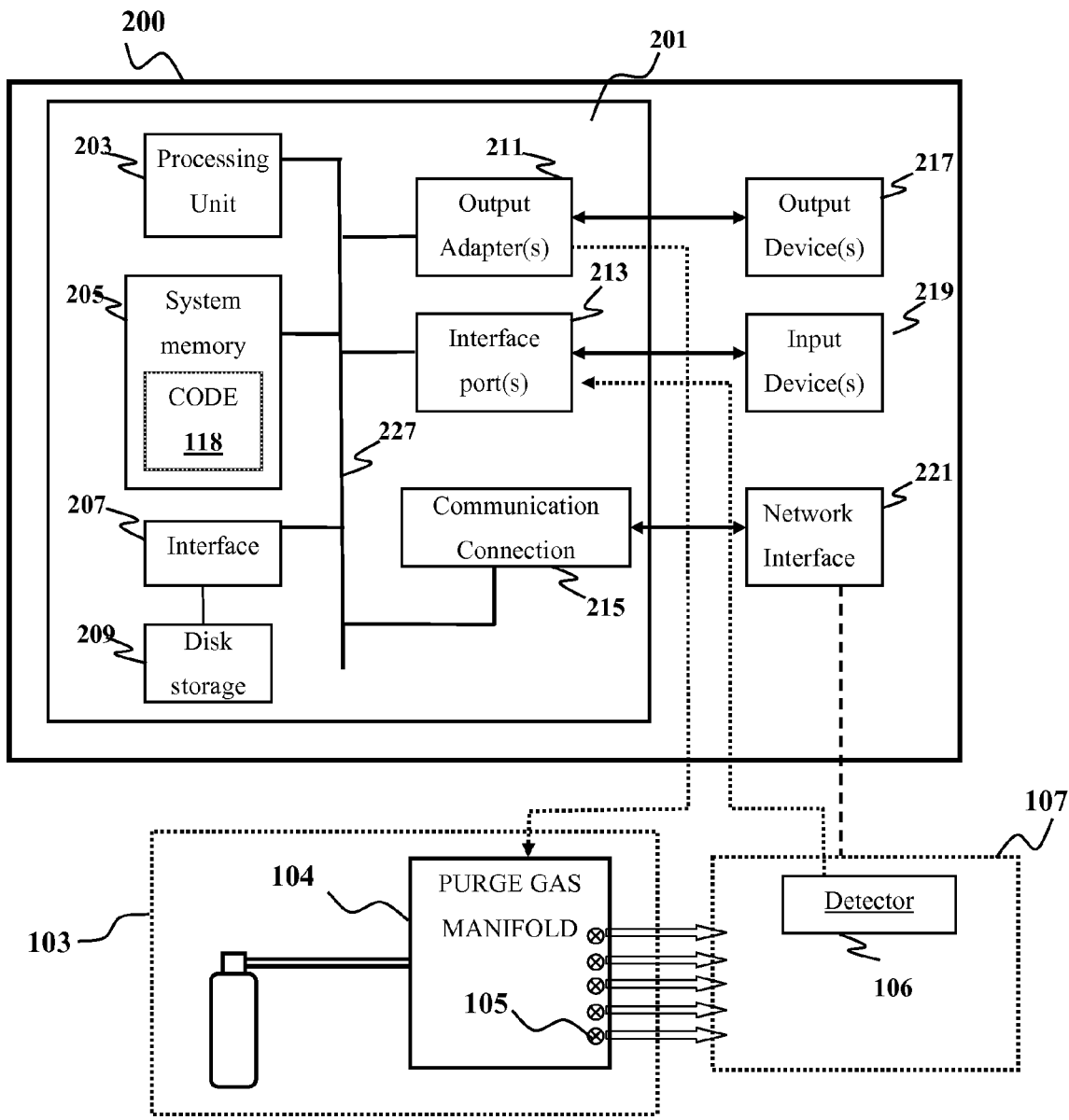
FIG. 2 is a block diagram illustrating a computing system in connection with facilitating employment of embodiments of the present invention.

FIG. 2 is a block diagram of an exemplary computing system 200 that may be used in connection with facilitating employment of the subject invention. The computing system 200 may implement the functions of the controller 116. With reference to FIG. 2, the computer system 200 includes a computer 201. The computer 201 includes a processing unit 203, a system memory 205, and a system bus 227. The system bus 227 couples system components including, but not limited to, the system memory 205 to the processing unit 203. The processing unit 203 can be any of various available processors.

The system bus 227 can be any of several types of bus structure(s) including the memory bus or memory controller, a peripheral bus or external bus, and/or a local bus using any variety of available bus architectures including, but not limited to, 11-bit bus, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Universal Serial Bus (USB), Advanced Graphics Port (AGP), Personal Computer Memory Card International Association bus (PCM-CIA), and Small Computer Systems Interface (SCSI).

The system memory 205 may include volatile memory and/or nonvolatile memory. The basic input/output system (BIOS), comprising the basic routines to transfer information between elements within the computer 201, such as during start-up, may be stored in nonvolatile memory. By way of illustration, and not limitation, nonvolatile memory may include read only memory (ROM), programmable ROM (PROM), electrically programmable ROM (EPROM), electrically erasable ROM (EEPROM), or flash memory. Volatile memory includes random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). The code instructions 118 may be stored in system memory 205 in the form of processor readable instructions that can be executed on the processing unit 203. The code instructions may include instructions that direct the purge gas source 103 to adjust the flow rate of purged gas into the focus housing 109, illumination optics housing 124, collection optics housing 120, the main housing 126 and detector housing 107.

The computer 201 may optionally include removable/non-removable, volatile/non-volatile computer storage medium 209, for example disk storage. Storage medium 209 may include, but is not limited to, devices like a magnetic disk drive, floppy disk drive, tape drive, Jaz drive, Zip drive, LS-100 drive, flash memory card, or memory stick. In addition, storage medium 209 may include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 209 to the system bus 227, a removable or non-removable interface is typically used such as interface 207.

The computer system 200 may also includes input devices 219 such as a pointing device such as a mouse, trackball, stylus, touch pad, keyboard, microphone, joystick, and the like. These and other input devices may connect to the processing unit 203 through the system bus 227 via interface port(s) 213. Interface port(s) 213 include, for example, a serial port, a parallel port, a game port, and a universal serial bus (USB). Output device(s) 217 use some of the same type of ports as input device(s) 219. Thus, for example, a USB port can be used to provide input to the computer 201 from the detector 106, and to output information from computer 201 to an output device 217 or to the purge gas source 103. Output adapter 211 is provided to illustrate that there are some output devices 217 like monitors, speakers, and printers, among other output devices 217, which may require special adapters. The output adapters 211 may include, by way of illustration and not limitation, video and sound cards that provide a means of connection between the output device 217 and the system bus 227.

The computer system 200 may also include a network interface 221 to enable the device to communicate with the metrology tool 102 and/or other devices over a network, e.g., a local area network or a wide area network, such as the internet. Communication connection 215 refers to the hardware/software employed to connect the network interface 221 to the bus 227. While communication connection 215 is shown for illustrative clarity inside computer 201, it can also be external to computer 201. The hardware/software necessary for connection to the network interface 221 includes, for exemplary purposes only, internal and external technologies such as, modems including regular telephone grade modems, cable modems and DSL modems, ISDN adapters, and Ethernet cards.

Figure 3A:
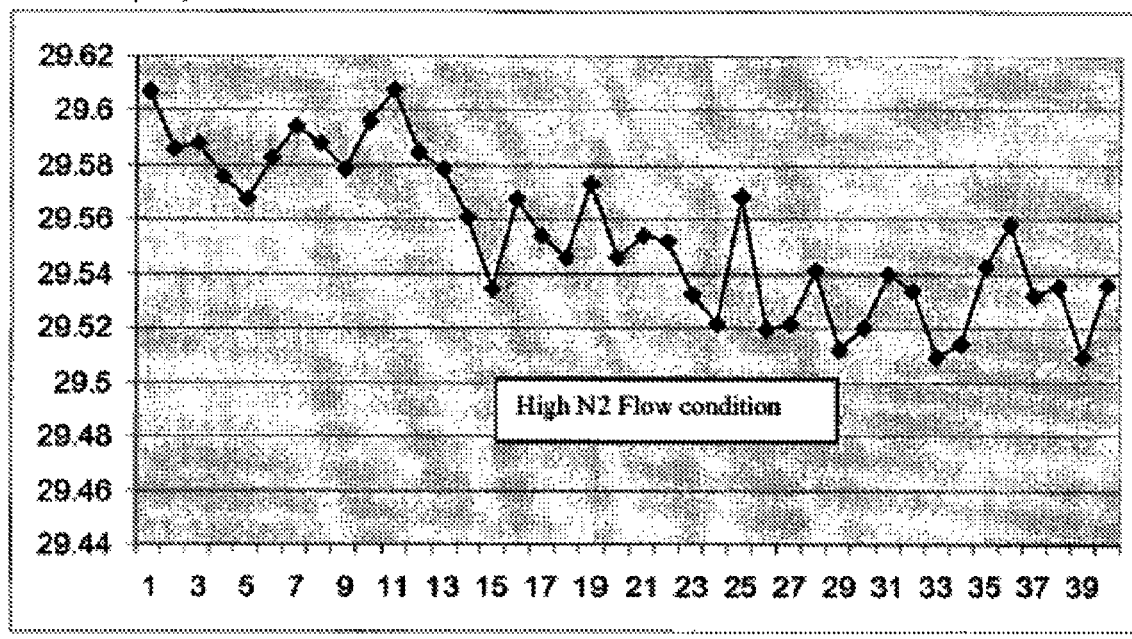
FIGS. 3A-3B are graphs illustrating the precisions of spectroscopic ellipsometry (SE) thickness measurements of a thin oxide with high and low Nitrogen flow conditions.
Figure 3B:
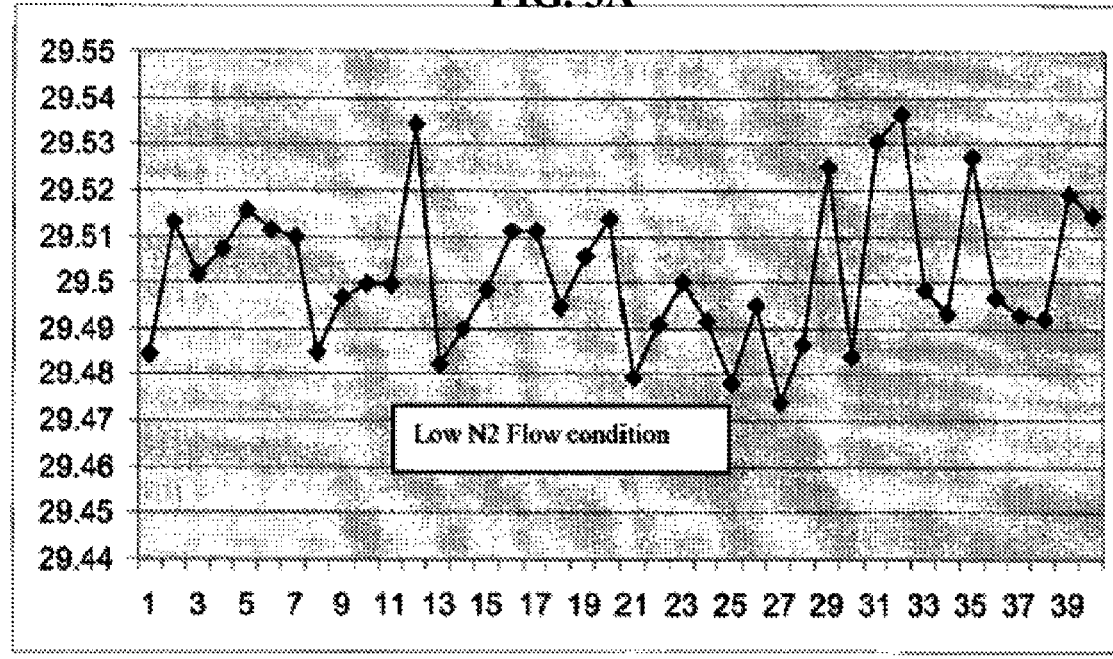

Prior art broadband spectroscopic ellipsometry (BBSE) systems currently use a local purging method in which a gas, such as nitrogen, flows only in volumes around the beam path. For an optical system of the type depicted in FIG. 1, purge gas may independently flow through the focus housing 109, illumination optics housing 124, collection optics housing 120, the main housing 126 and detector housing 107. However, as indicated above, there is an interaction between the purging nitrogen gas and atmospheric molecular contaminants (AMC) on the surface of the sample, which results in a change in effective thickness of the AMC layer on a wafer during film thickness measurements performed in the UV-Vis spectral region, causing the reported precision of the SE measurements to be higher. FIGS. 3A-3B are graphs showing 30 points thin oxide SE thickness measurements with high and low $N_2$ flow conditions. With reference to FIG. 3A, the flow rates of the main housing, illuminator optics housing, collector optics housing, focus housing and spectrometer housing are 5(12.9)-4-4-4-4 (liter/min) respectively. As shown in this figure, the thickness of the thin oxide drifts down as the number of measurements increases due to AMC being cleaned by high $N_2$ flow. In FIG. 3B, the flow rates of the main housing, illuminator optics housing, collector optics housing, focus housing and spectrometer housing are 1(2.96)-1-1-1-1 (liter/min) respectively. As shown in FIG. 3B, the thickness of the thin oxide film drifts negligibly with lower $N_2$ flow rates due to the AMC layer being stabilized in a short time, resulting in higher precision and repeatability of SE measurement in UV-Vis spectral region.

Figure 4A:
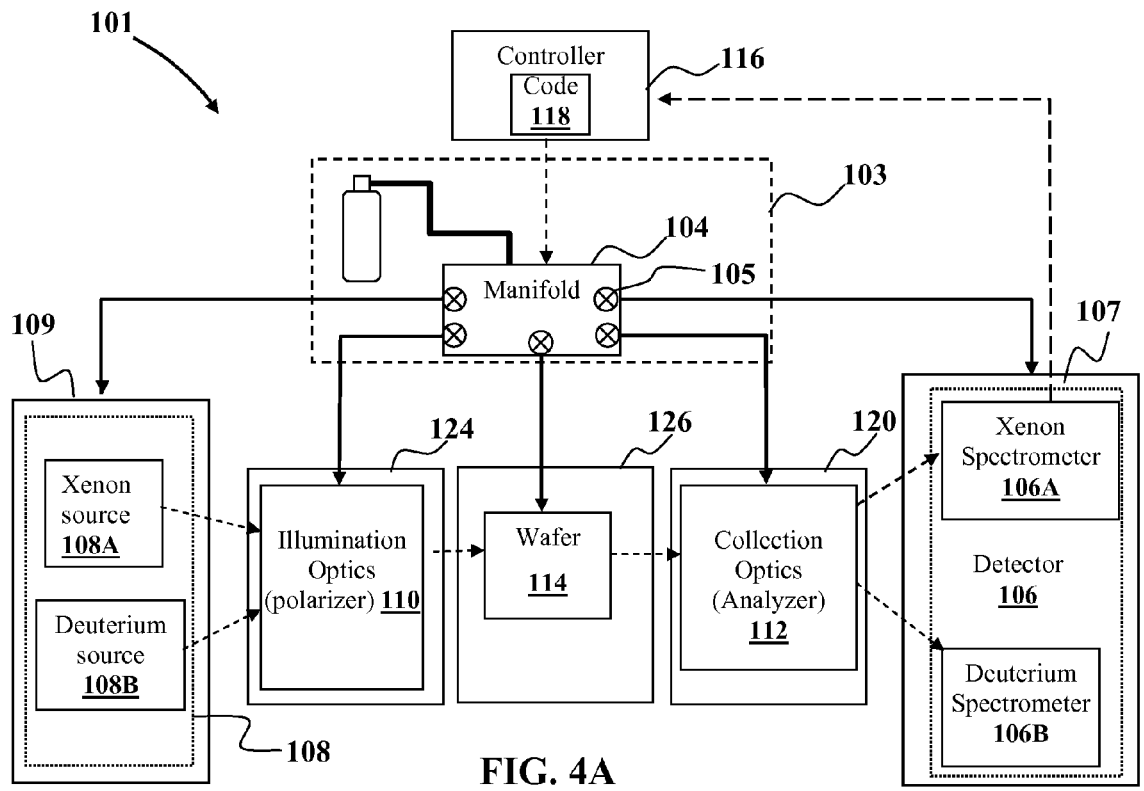
FIG. 4A is block diagram illustrating an alternative layout of an optical system of the type depicted in FIG. 1.
Figure 4B:
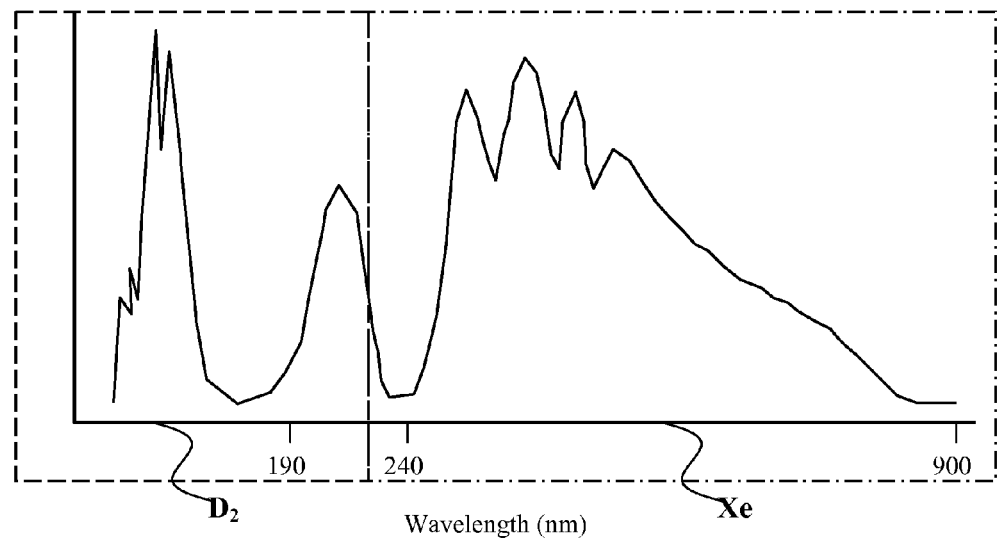
FIG. 4B is a graph depicting emission spectra for Deuterium and Xenon light sources.

FIG. 4A is a block diagram illustrating a different layout 101 of the optical system 100 described in FIG. 1. As shown in FIG. 4A, nitrogen gas from source 103 having a manifold 104 and valves 105 is independently purged in the focus housing 109, illumination optics housing 124, collection optics housing 120, the main housing 126 and detector housing 107. Nitrogen gas is purged in high flow rates to enable metrology measurement of the wafer 114 in VUV spectral region below about 200 nm (including, e.g., from about 120 nm to about 190 nm). A light source 108 located in a focus housing 109 illuminates a beam of radiation on a spot of the wafer 114 located in a main housing 126 through illumination optics 110 located in the illumination optics housing 124. The light source 108 preferably contains deuterium and xenon lights to provide wavelengths in VUV and UV-Vis ranges as shown in FIG. 4B. Collection optics 112 collects the radiation of the beam scattered from the wafer and provides collected radiation to the detector 106. A VUV output of detector 106, which is a deuterium spectrum, is sent to the controller 116 for analysis. In response to the VUV output from the detector 106, the code instruction 118 stored in the controller 106 directs nitrogen source 104 to reduce the nitrogen flow rates to the focus housing 109, illumination optics housing 124, collection optics housing 120, the main housing 126 and detector housing 107 to enable metrology measurement of the wafer 114 in a UV-Vis range between about 200 nm and about 900 nm. By way of example, the light source 108 may contain a deuterium source 108A to produce source radiation in the VUV region and a xenon source 108B to produce source radiation in the UV-Vis range. The detector 106 may include separate spectrometers 106A, 106B for Deuterium and Xenon radiation respectively.

Figure 5:
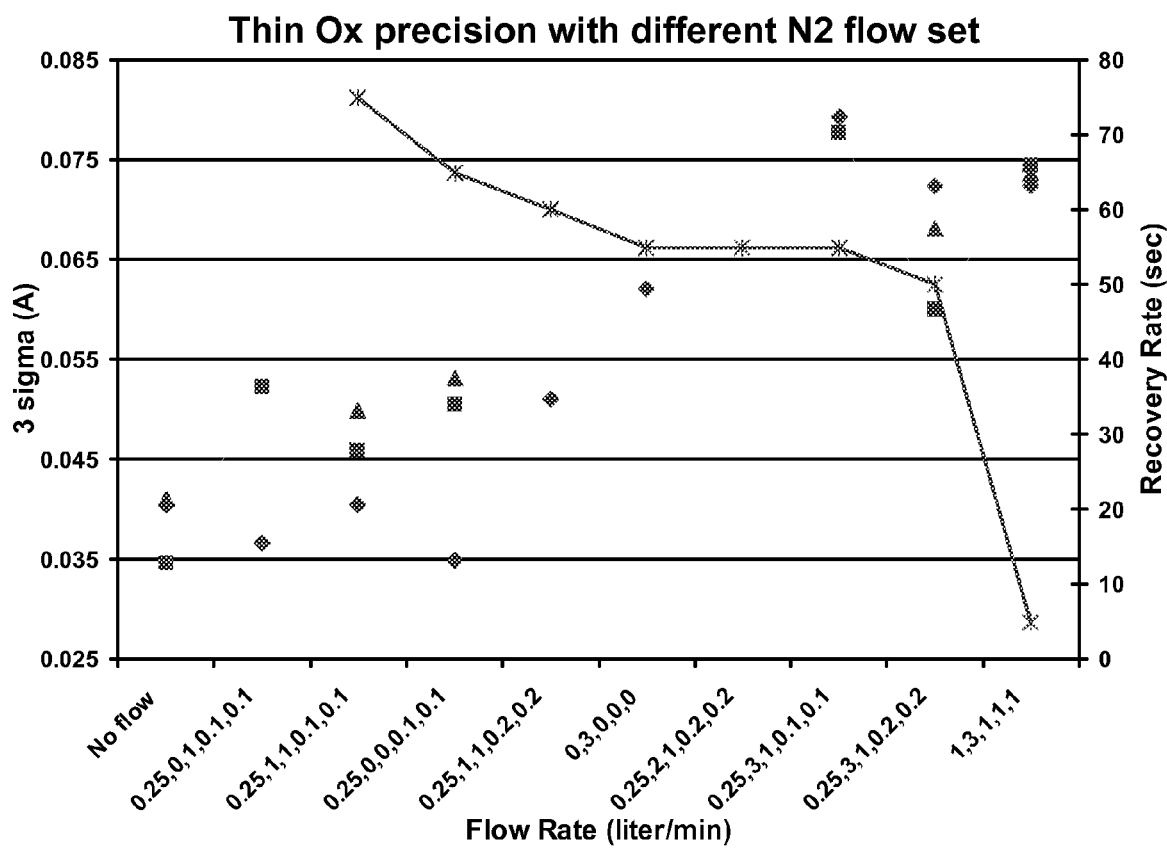
FIG. 5 is a graph showing the thin oxide precision and recovery time of VUV signal with different Nitrogen flow sets.

Lowering $N_2$ flow rates during the metrology measurement in the UV-Vis spectral region is acceptable since VUV radiation is not used in the measurement and is blocked in the illuminator optics 110. However, if the $N_2$ flow rates are low and stay low for long durations, the overall purging quality may be degraded. The degree of degradation is partly a function of the duration of the reduced flow and the magnitude of the reduced $N_2$ flow rate. Depending on the initial flow rates in the low flow mode, the recovery time of VUV signal, when the $N_2$ flow changed to high flow rates, can vary. For example FIG. 5 is a graph showing the precision of thin oxide SE thickness measurements and the recovery time of the VUV signal with different $N_2$ flow sets. The diamonds, squares and triangles represent precision for the thickness measurements for different flow sets. The solid line shows the recovery time for the same flow sets. Each flow set shows $N_2$ flow rates, in liters/per minute, for the main housing, illuminator optics housing, collector optics housing, focus housing and spectrometer housing, respectively. By way of example, the flow set (0.25, 0, 1, 0.1, 0.1) represents a flow rate of 0.25 liters per minute for the main housing, 0 liters/min (no flow) through the illuminator optics housing, 0.1 liter/min through the collector optics housing, 0.1 liters/min through the focus housing and 1 liters/min through the spectrometer housing.

As shown in FIG. 5, if the $N_2$ flow is shut down while performing SE measurement in the UV-Vis spectral region, the recovery rate of the VUV signal may be too long for practical applications. If the flow rates are too high, the precision may be above an acceptable level specified for a given application. However, by appropriate adjustment of the flow rates and balancing the effects of flow rate on recovery time and SE measurement precision, an optimum may be achieved that meets the precision specification and has an acceptable recovery time. For example, a recovery time of about 1 min is reasonable for many applications. From FIG. 5 it is shown that a 3 sigma precision spec of about 0.06 Angstroms may be achieved at a recovery time of about 1 min.

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. Any feature, whether preferred or not, may be combined with any other feature, whether preferred or not. In the claims that follow, the indefinite article "A", or "An" refers to a quantity of one or more of the item following the article, except where expressly stated otherwise. The appended claims are not to be interpreted as including means-plus-function limitations, unless such a limitation is explicitly recited in a given claim using the phrase "means for."

What is claimed is:

1. An optical method for measuring characteristics of a sample using a broadband metrology tool in a purge gas flow environment, comprising:
   purging a beam path for the metrology tool with purge gas at a first flow rate;
   illuminating a surface of the sample by a beam of source radiation, the beam comprising at least one wavelength component in a vacuum ultraviolet (VUV) range and/or at least one wavelength component in a ultraviolet-visible (UV-Vis) range; and
   adjusting a flow rate of a purge gas between the first flow rate for metrology measurements made when the source radiation is in the VUV range and a second flow rate for metrology measurements made when the source radiation is in the UV-Vis range.

2. The method of claim 1, wherein adjusting the flow rate of the purge gas includes lowering the flow rate so that the second flow rate is lower than the first flow rate.

3. The method of claim 2, wherein adjusting the flow rate of the purge gas includes monitoring an effect of the flow rate on an Airborne Molecular Contaminants (AMC) layer on a surface of the sample using measurements taken with the metrology tool.

4. The method of claim 3 wherein adjusting the flow rate includes varying the flow rate in a manner that stabilizes a thickness of AMC layer.

5. The method of claim 4 wherein adjusting the flow rate includes monitoring a precision of the metrology measurements and varying the flow rate in a manner that optimizes a precision of measurements taken with the metrology tool using source radiation in the UV-Vis range.

6. The method of claim 1, wherein the metrology tool is a spectroscopic ellipsometer, single-wavelength ellipsometer, spectroscopic reflectometer or single-wavelength reflectometer.

7. The method of claim 1, wherein adjusting of a flow rate of the purge gas includes increasing the flow rate of the purge gas for a metrology tool measurement using source radiation in the VUV spectral region after a measurement taken with the metrology tool using source radiation in the UV-Vis region, whereby the first flow rate is greater than the second flow rate.

8. The method of claim 7 wherein adjusting of a flow rate of the purge gas includes monitoring a VUV signal measured with the metrology tool and optimizing a recovery time of the VUV signal measured with the metrology tool.

9. The method of claim 8 wherein the recovery time is about 60 seconds or less.

10. An optical system for measuring characteristics of a samples using a broadband metrology tool in a purged gas flow environment, comprising:

a light source configured to supply a beam of source radiation having at least one wavelength component in a VUV range and/or at least one wavelength component in a UV-Vis range;

illumination optics adapted to illuminate a surface of the sample with the beam source of radiation;

collection optics collecting signal radiation generated by interaction of the beam source radiation with the surface of the sample;

a detector adapted to provide at least one output signal in response to the signal radiation collected from the collection optics, wherein the signal is related to a property of the surface of the sample;

a purge gas source configured to supply a flow of purge gas to a beam path in the light source and/or illumination optics and/or sample and/or collection optics and/or detector; and a controller operably coupled to the detector and the purge gas source, wherein the controller is configured to control a flow rate of the purged gas flow in response to the output signal from the detector by adjusting a flow rate of the purge gas between a first flow rate for metrology measurements made when the source radiation is in the VUV range and a second flow rate for metrology measurements made when the source radiation is in the UV-Vis range.

11. The system of claim 10 wherein the controller includes an interface unit that facilitates interaction between the detector, the purge gas source and the controller.

12. The system of claim 11, wherein the controller includes a processor and a system memory.

13. The system of claim 10, wherein the illumination optics comprises a polarizer.

14. The system of claim 10, wherein the collection optics comprises an analyzer.

15. The system of claim 10 wherein the detector is a spectroscopic ellipsometer or single-wavelength ellipsometer.

16. The system of claim 10 wherein the detector is a spectroscopic reflectometer or single-wavelength reflectometer.

17. The system of claim 10 wherein the purge gas does not substantially absorb VUV radiation.

18. The system of claim 17 wherein the purge gas is selected from the group of nitrogen, helium, argon, neon and other inert gases.

19. The system of claim 18, wherein the purge gas source includes a gas manifold coupled to two or more of the light source, illumination optics, sample, collection optics and/or detector through separate gas lines, each gas line having a valve operably coupled to the controller, whereby the controller is configured to control separate flows of purge gas to two or more of the light source, illumination optics, sample, collection optics and/or detector.

20. The system of claim 10, wherein the controller is operably coupled to the light source, wherein the controller is configured to purge a beam path for the metrology tool with purge gas at a first flow rate;

illuminate a surface of the sample by a beam of source radiation, the beam comprising at least one wavelength component in a vacuum ultraviolet (VUV) range and/or at least one wavelength component in a ultraviolet-visible (UV-Vis) range; and adjust the flow rate of the purge gas between the first flow rate for metrology measurements made when the source radiation is in the VUV range and the second flow rate for metrology measurements made when the source radiation is in the UV-Vis range.

* * * * *